United States Patent [19]

Bauman

[11] 4,046,873
[45] Sept. 6, 1977

[54] ALICYCLIC AMIDO-QUATERNARY AMMONIUM ANTI-BACTERIAL AGENTS

[75] Inventor: Robert Andrew Bauman, New Brunswick, N.J.

[73] Assignee: Colgate Palmolive Company, New York, N.Y.

[21] Appl. No.: 445,713

[22] Filed: Feb. 25, 1974

Related U.S. Application Data

[63] Continuation-in-part of Ser. No. 400,097, Sept. 24, 1973, Pat. No. 3,928,411, which is a continuation of Ser. No. 39,536, May 21, 1970, abandoned.

[51] Int. Cl.$^2$ .................... A61K 7/22; A61K 31/14; C07C 87/40
[52] U.S. Cl. .................... 424/54; 260/404.5; 260/501.15; 260/557 B; 424/320
[58] Field of Search .................... 260/557 B, 501.15; 424/320, 329, 54

[56] References Cited

U.S. PATENT DOCUMENTS

| | | | |
|---|---|---|---|
| 2,681,931 | 6/1954 | Jenkins | 260/557 B |
| 3,374,244 | 3/1968 | Krimmel | 260/557 B X |
| 3,578,667 | 5/1971 | Wakeman et al. | 260/501.15 X |
| 3,709,937 | 1/1973 | Krimmel | 260/557 B |
| 3,898,284 | 8/1975 | Bauman | 260/501.15 X |
| 3,907,895 | 9/1975 | Bauman | 260/501.15 X |
| 3,928,411 | 12/1975 | Bauman | 260/557 B X |
| 3,953,605 | 4/1976 | Bauman | 424/54 X |
| 3,956,479 | 5/1976 | Bauman | 424/54 |
| 3,961,074 | 6/1976 | Bauman | 424/54 |
| 3,961,075 | 6/1976 | Bauman | 424/54 |

*Primary Examiner* — Daniel E. Wyman
*Assistant Examiner* — Thomas A. Waltz
*Attorney, Agent, or Firm* — Robert L. Stone; Murray M. Grill; Herbert S. Sylvester

[57] ABSTRACT

Novel quaternary ammonium compounds containing two large aliphatic or alicyclic groups, one of which is separated from the quaternary nitrogen by an amide linkage.

8 Claims, No Drawings

ALICYCLIC AMIDO-QUATERNARY AMMONIUM ANTI-BACTERIAL AGENTS

The present application is a continuation-in-part of copending application serial U.S. 400,097, filed Sept. 24, 1973, now U.S. Pat. No. 3,928,411 granted Dec. 23, 1975, which is a continuation of U.S. Pat. application Ser. No. 39,536 filed May 21, 1970, now abandoned.

The present invention relates to novel quaternary ammonium compounds represented by the general formula:

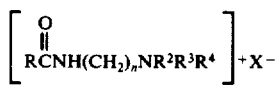

wherein R is an aliphatic or alicyclic group containing 7-13 carbon atoms, $R^2$ and $R^3$ are each methyl or ethyl, $R^4$ is an aliphatic chain containing 10-18 carbon atoms, n is the integer 2 or 3 and X is a compatible anion such as the halides (Cl-,Br-,I-), sulfates (i.e., methyl sulfate), nitrates, aryl sulfonates, etc. These quaternary compounds possess superior antimicrobial, anticaries, and anticalculus activity.

The alicyclic group may be any ring system such as the adamantyl radical which is derived from tricyclo-[3.3.1.1$^{3,7}$]decane showing four fused chain cyclohexane rings as follows:

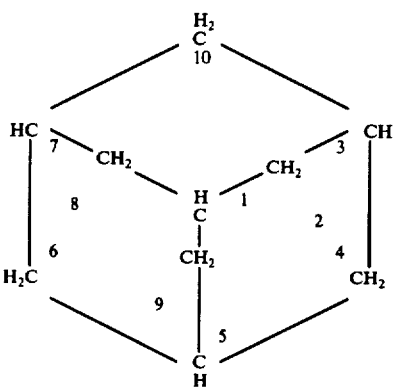

a bicyclo [3.3.0] octane showing two joined pentane rings as follows:

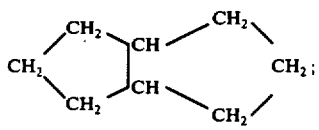

the norbornane radical which is represented by the following ring structure:

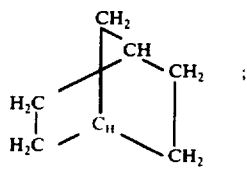

or any other aliphatic ring system containing 7 to 13 carbon atoms.

Typical examples of the quaternary ammonium compounds which may be used in this invention are:
1. 3-Heptaneamidopropyldimethyltetradecyl ammonium chloride,
2. 3-Decaneamidopropyldimethyltetradecyl ammonium chloride,
3. 3-Octaneamidopropyldimethyldecyl ammonium iodide,
4. 3-Octaneamidopropyldimethyldodecyl ammonium iodide,
5. 3-Octaneamidopropyldimethyltetradecyl ammonium chloride,
6. 3-Nonaneamidopropyldimethyltetradecyl ammonium chloride,
7. 3-Dodecaneamidopropyldimethyltetradecyl ammonium chloride,
8. 3-Undecaneamidopropyldimethyltetradecyl ammonium chloride,
9. 3-(1'-adamantanecarboxamido)propyldimethyldodecyl ammonium bromide,
10. 3-(1'-adamantanecarboxamido)propyldimethyltetradecyl ammonium bromide,
11. 3-(1'-adamantanecarboxamido)propyldimethyltetradecyl ammonium chloride,
12. 2-(1'-adamantanecarboxamido)ethyldiethyldecyl ammonium bromide,
13. 2-(1'-adamantanecarboxamido)ethyldiethyldodecyl ammonium bromide.
14. 3-(exo,cis-Bicyclooctane-2-carboxamido)propyltetradecyl dimethyl ammonium bromide,
15. 3-(exo,cis-Bicyclooctane-2-carboxamido)propyldodecyldimethyl ammonium bromide,
16. 3-(2'-norbornanecarboxamido)propyltetradecyldimethyl ammonium bromide.

Other halides and analogous compounds such as the sulfates, nitrates, aryl sulfonates, etc. may also be employed herein as effective bactericides.

It has been observed that the compounds generally described by the foregoing formula are particularly effective against gram positive organisms such as *Staphylococcus aureus; Streptococcus mitis,* sanguis and mutans; *Bacillus subtilis; Corynbacterium acnes; Actinomycetes naeslundii;* and against fungi, such as *Candida albicans,* Trichophyton mentogrophytes and Aspergillus niger; and moderately effective against *Escherichia coli* which is a gram negative bacteria. Compounds wherein $R^4$ is a benzyl radical in lieu of instant higher alkyl radical are devoid of antibacterial activity.

The anti-microbial nature of the instant novel compounds was shown by a standard test tube serial dilution test in which an appropriate number of test tubes of broth containing decreasing concentrations of the test agent was innoculated with the test organism. After a suitable period of incubation, the tubes were examined for the presence or absence of growth. The activity of the test agent was the lowest concentration which inhibited the growth of the organism and is expressed as the minimal inhibitory concentration in ppm. As shown in the following table of antimicrobial data, a definite break occurs between compounds wherein $R^4$ contains 8 carbons and 10 carbons.

TABLE I

Minimum Inhibitory Concentration (ppm)

$$\left[\text{(adamantyl)}\text{CONHCH}_2\text{CH}_2\text{N}(\text{C}_2\text{H}_5)_2\text{R}^4\right] \text{Br}$$

| | $R^4 = C_4H_9$ | $C_6H_{13}$ | $C_8H_{17}$ | $C_{10}H_{21}$ | $C_{12}H_{25}$ |
|---|---|---|---|---|---|
| S. aureus | 100 | 100 | 25 | 3.12 | 1.56 |
| Str. sanguis | 50 | 50 | 50 | 6.25 | 3.12 |
| Str. mutans | 100 | 100 | 25 | 6.25 | 0.78 |
| A. naeslundii | 100 | 50 | 12.5 | 1.56 | 0.39 |
| C. albicans | 100 | 100 | 50 | 6.25 | 1.56 |
| T. mentagrophytes | 50 | 50 | 50 | 50 | 3.12 |
| A. niger | 100 | 100 | 100 | 50 | 12.5 |

These dilution tests evidence the effectiveness of compounds of the invention against bacteria and fungi not possessed by amidoquaternary ammonium compounds containing 3 lower aliphatic radicals.

When used against bacteria or fungi, compounds of the instant invention may be applied directly to the surface to be protected or may be dissolved in a pharmaceutical carrier. Typically, an effective amount, e.g., 0.025 to about 10% by weight of the compound, is included in an inert carrier and a dispersing or surface-active agent. Alternatively, an effective amount, e.g. 0.025 to about 10% by weight may be incorporated into a solid carrier which may be inert, such as talc, clay, diatomaceous earth, flour, etc.

The quaternary ammonium amides of adamantanecarboxylic acid are particularly effective in inhibiting the development of dental calculus as shown by the results of tests on littermated albino rats, in groups of 15 males and 15 females who were fed a Zipkin-McClure calculus producing diet. For six weeks the teeth of each animal were swabbed for thirty seconds each day with a test solution or water for the control group. The animals were then sacrificed, defleshed and scored by Baer's method for calculus. The results were analyzed by Student's $t$ test and in the results quoted were 99% significant.

| Compound | Concentration Test Solution | Calculus Reduction % | |
|---|---|---|---|
| | | Males | Females |
| 3-(1'-adamantane-carboxamido) propyl tetradecyl dimethyl ammonium bromide | .1% | 43.43 | 6.27 |

The results set forth above indicate the significant effectiveness of the quaternary compounds of the invention in inhibiting formation of oral calculus in concentrations as low as 0.1%.

When compounds of the instant invention are intended for use in compositions which reduce formation of caries and inhibit formation of oral calculus, they are typically incorporated in oral preparation in effective amounts up to about 5% by weight, preferably 0.025–1% and most preferably 0.25–0.5% by weight of the oral preparation. Typically, the oral preparation is a dentifrice, such as a dental cream, tablet or powder, containing as a vehicle about 20–95% by weight of a water-insoluble polishing material, preferably including water-insoluble phosphate such as dicalcium phosphate, tricalcium phosphate, trimagnesium phosphate. The dentifrice may also include water; binders such as glycerine, sorbitol, propylene glycol and polyethylene glycol 400; detergents, gelling agents such as Irish moss and sodium carboxy methyl cellulose; additional antibacterial agents; coloring or whitening agents; preservatives; silicones; chlorophyll compounds; additional ammoniated materials; flavoring or sweetening materials; and compounds which provide fluorine-containing ion such as sodium fluoride, stannous fluoride and sodium monofluorophosphate.

The oral preparation may also be a liquid such as mouth rinse which typically contains 20–99% by weight of an aqueous lower aliphatic alcohol, preferably having about 1–30% by weight alcohol such as ethanol, n-propyl, or isopropyl alcohol.

Such oral preparations are typically applied by brushing the teeth or rinsing the oral cavity for 30–90 seconds at least once daily. Typical oral preparations of the invention which can be applied in this manner are set forth below.

EXAMPLE 1

Dental Cream

| | % |
|---|---|
| 3-Decaneamidopropyldimethyltetradecyl ammonium chloride | 0.50 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |
| Water | 22.15 |

*Tween 80-Polyoxyethylene (20 moles ethylene oxide) sorbitan monooleate.

EXAMPLE 2

Mouthwash

| | % |
|---|---|
| Quaternary ammonium amide of adamantane carboxylic acid | 0.025 |
| Nonionic detergent (Pluronic F-68)* | 1.00 |
| Ethyl alcohol (containing flavor) | 15.00 |
| Glycerine | 10.00 |
| Saccharin | 0.02 |
| Water | 73.73 |

*Block polymer of 80% polyoxyethylene and 20% polyoxypropylene.

The quaternary ammonium amides of instant invention can be prepared by a two-step method of reacting a carboxylic acid, ester or acid chloride with N,N-dialkylethylene diamine or N,N-dialkylpropylene diamine to form a tertiary amino amide and subsequently quaternizing with an alkyl halide or ester of sulfuric or of arenesulfonic acid (i.e., methyl p-toluenesulfonate) as illustrated by the following equations wherein R, $R^2$, $R^3$, $R^4$ have the aforedefined meanings.

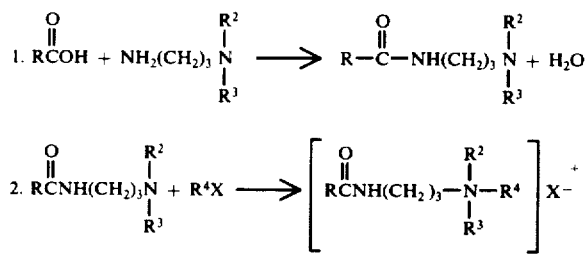

The following examples illustrate the manner in which compounds of this invention are prepared.

EXAMPLE 3

Preparation of 3-(1'-adamantanecarboxamido)propyl-dodecyl-dimethylammonium bromide: 2.5 grams of N,N-dimethyl-1,3-propane diamine was added to a cold solution of 5 grams 1-adamantane carboxylic acid chloride in 15 cc benzene. An immediate precipitate formed. The mixture was stirred and permitted to sit for thirty minutes. The precipitate was washed with benzene several times, centrifuged, and dried in vacuum, yielding 5 grams of N-(3-dimethylaminopropyl)adamantane-1-carboxamide hydrochloride having a melting point of 154°-157° C. This product was dissolved in 150 cc acetone, placed in a refrigerator for crystal growth and 4.8 gms of the product was recovered.

This hydrochloride was dissolved in 100 cc water and 25 cc of 1N NaOH was added. A white precipitate formed which was extracted with ether, dried by flash evaporation and 3.2 grams of the free base having a melting point of 78°-80° C was recovered. The infrared spectrum confirmed the structure of this product.

The aforedefined reaction product was quaternized by reacting 1.6 grams (.06 mole) of N-(3-dimethylaminopropyl)-1-adamantanecarboxamide with 1.5 grams (.06 mole) of 1-bromododecane dissolved in 4 cc acetone. After standing for two weeks, the reaction mixture was chilled with dry ice. The resultant crystalline mass was washed with ether, dried in vacuum, and recrystallized from ethyl acetate, giving a crystalline product having a melting point of 122°-124° C and the following analysis:

|  | Found | Calculated |
|---|---|---|
| Carbon | 64.81 | 65.47 |
| Hydrogen | 10.84 | 10.40 |
| Molecular weight: 513.66 | | |

EXAMPLE 4

The tetradecyl homolog of the above carboxyamide was prepared in accordance with the process of Example 3. The recovered crystals had a melting point of 120°-122° C and the following analysis:

|  | Found | Calculated |
|---|---|---|
| Carbon | 65.80 | 66.52 |

|  | Found | Calculated |
|---|---|---|
| Hydrogen | 10.54 | 10.61 |
| Molecular weight: 541.71 | | |

EXAMPLE 5

Preparation of 3-Decanamidopropyldimethyltetradecylammonium chloride: A solution of 102 g (1 mol) N,N-dimethylpropylene diamine in 400 ml benzene was stirred during the addition of 95.3 g (0.5 mol) decanoyl chloride and kept below 50° C with an ice bath. After standing overnight at room temperature, the reaction mixture was poured into 1 liter of 2% sodium hydroxide solution. The benzene layer was separated and combined with four subsequent 100 ml ether extracts of the aqueous layer. The organic solution was washed with water and dried over sodium sulfate. Vacuum evaporation left 116.5 g oil (91% yield). Infrared and nmr spectra showed the product to be N-(3-dimethylaminopropyl)decamide.

26 g (0.1 mole) of the above amino amide was mixed with 23 g (0.1 mole) 1-chlorotetradecane and maintained in an oven at 100° C for 70 hours. The reaction mixture was cooled to room temperature, washed with ether and recrystallized successively from acetone and ethyl acetate, giving a crystalline monohydrate product having a melting point of 55°-57° C to liquid crystal, and 173° C to liquid. Upon drying said monohydrate at 75° C, a hygroscopic anhydrous form is obtained. This product, calculated for $C_{29}H_{61}ClN_2O \cdot H_2O$ has the following analysis:

|  | Found | Calculated |
|---|---|---|
| Carbon | 69.09 | 68.66 |
| Hydrogen | 12.66 | 12.52 |
| Nitrogen | 5.59 | 5.52 |
| Chlorine | 6.98 | 6.99 |

EXAMPLE 6

3-(exo,cis-Bicyclo[3.3.0]octane-2-carboxamido)propyl-tetradecyldimethylammonium bromide To a solution of 23 g exo,cis-bicyclo[3.3.0]octane-2-carboxylic acid (Organic Syntheses 47 10) in 100 ml benzene was added 12 ml thionyl chloride and 1 ml dimethyl formamide. The reaction mixture was stirred 15 minutes at room temperature and then dry nitrogen gas was bubbled through the solution for 30 minutes to remove HCl. The solution of acid chloride was transferred to a dropping funnel and slowly added to a stirred solution of 34 g N,N-dimethylpropylenediamine in 100 ml benzene at 20°-25° C.

After 30 minutes, the reaction was worked up by pouring into sodium hydroxide solution and extracting the product with ether. Hydrochloric acid solution was added for neutralization and again extracted with ether. Evaporation of the ether left 31 g of a crystalline solid (86% of theory). Recrystallized from hexane, it melted at 60°-63° C.

Analysis - Neutral equivalent: Calcd, 238.4 Found, 241.3

A mixture of 12 g of the above compound and 14 g 1-bromotetradecane in 100 ml acetone was refluxed for 24 hours. On chilling, 20.4 g (78% of theory) crystals separated. After crystallizing from acetone, the compound melted at 119°–122° C.

Analysis: Based on $C_{28}H_{55}BrN_2O$:

|  | Calculated | Found |
|---|---|---|
| Carbon | 65.21 | 65.05 |
| Hydrogen | 10.75 | 10.81 |
| Bromine | 15.50 | 15.26 |
| Nitrogen | 5.43 | 5.21 |

EXAMPLE 7

3-(exo,cis-Bicyclo[3.3.0]octane-2-carboxamido)propyl-dodecyldimethylammonium bromide Prepared by the same procedure as in Example 6, this compound melted at 119°–120.5° C.

Analysis: Based on $C_{26}H_{51}BrN_2O$:

|  | Calculated | Found |
|---|---|---|
| Carbon | 64.04 | 64.01 |
| Hydrogen | 10.54 | 10.64 |
| Bromine | 16.39 | 16.21 |
| Nitrogen | 5.75 | 5.57 |

EXAMPLE 8

3-(2'-Norbornanecarboxamido)propyltetradecyldimethylammonium bromide

Prepared by a similar procedure as in Example 6 starting with 2-norbornanecarboxylic acid chloride. Recrystallized from ethyl acetate, the compound melted at 129°–131° C.

Analysis: Bromide: Calc. 15.93%. Found, 15.61%.

The superior and unexpected antimicrobial activity exhibited by the novel compounds of instant invention is clearly shown by the antimicrobial results in Tables II and III.

possess unexpectedly superior antimicrobial properties not present in prior art quaternary ammonium compounds (compound 1 in Table III, and first 3 compounds in Table I).

Although this invention has been described with reference to specific examples, it will be apparent to one skilled in the art that various modifications may be made thereto which fall within its scope.

I claim:

1. A chemical compound having the structural formula:

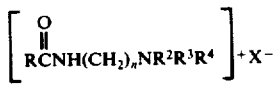

wherein R is an alicyclic group seclected from the group consisting of an adamantyl group, a bicyclooctane group and a norborane group, $R^2$ and $R^3$ are independently a methyl or ethyl group, $R^4$ is an alkyl chain consisting of 10–18 carbon atoms, n is the integer 2 or 3 and X is an anion selected from the group consisting of halides, sulfates, nitrates and arylsulfonates.

2. A chemical compound as set forth in claim 1, wherein R is an adamantyl group.

3. A chemical compound as set forth in claim 1, wherein R is bicyclooctane.

4. A chemical compound as set forth in claim 1, wherein R is norbornane.

5. A chemical compound as set forth in claim 1, wherein X is a halide.

6. 3-(1'-adamantanecarboxamido)propyltetradecyldimethylammonium bromide.

7. A composition comprising an effective antimicrobial amount of the compound of claim 1 admixed with a pharmaceutical carrier.

8. A composition comprising an effective antimicrobial amount of the compound of claim 1 admixed with an oral preparation.

TABLE II

| Microbe | Minimum Inhibitory Concentration (ppm) | | | | | |
|---|---|---|---|---|---|---|
|  | Comp.3 | Comp.14 (Ex.6) | Comp.15 (Ex.7) | Comp.16 (Ex.8) | Comp.9 (Ex.3) | Comp.10 (Ex.4) |
| S. aureus | 12.5 | 0.78 | 1.56 | 1.56 | 0.78 | 0.39 |
| Str. sanguis | 6.25 | 6.25 | 3.12 | 1.56 | — | — |
| Str. mitis | — | — | — | — | 0.39 | 0.39 |
| Str. mutans | 0.78 | <0.05 | 0.1 | 0.1 | — | — |
| A. naeslundii | 12.5 | <0.05 | 0.19 | 0.1 | — | — |
| E. coli | 50. | 50 | 25 | 50 | 50.0 | 25.0 |
| P. aeruginosa | 25 | 50 | 25 | 50 | — | — |
| C. albicans | 6.25 | 3.12 | 3.12 | 3.12 | 6.25 | 6.25 |
| T. mentagrophytes | 12.5 | 3.12 | 6.25 | 6.25 | 12.5 | 25.0 |
| A. niger | 25 | 25 | 25 | 25 | 25.0 | 50.0 |

TABLE III

| | | | [R CONH(CH$_2$)$_3$ N(CH$_3$)$_2$ R$^4$] X | | | | |
|---|---|---|---|---|---|---|---|
| | R | R$^4$ | X | S.aureus | S.mitis | E.coli | C.albicans | J.mentagrophyte |
| 1. | C$_{11}$ | C$_1$ | I | 50 | 50 | 50 | 50 | 50 |
| 2. | *C$_7$ | (branch) C$_{12}$ | I | 1.56 | 3.12 | 50 | 3.12 | 12.5 |
| 3. | *(C$_4$H$_9$) | (C$_2$H$_5$) C$_{12}$ | CH I | 0.78 | 1.56 | 12.5 | 1.56 | 12.5 |
| 4. | *C$_7$ | (branch) C$_{14}$ | Cl | .78 | 1.56 | 50 | 3.12 | 6.25 |
| 5. | C$_7$ | C$_{14}$ | Cl | .78 | 1.56 | 50 | 3.12 | 3.12 |
| 6. | C$_8$ | C$_{14}$ | Cl | 1.56 | 0.78 | 100 | 1.56 | 3.12 |
| 7. | C$_9$ | C$_{14}$ | Cl | 3.12 | 6.25 | 100 | 3.12 | 6.25 |
| 8. | C$_{11}$ | C$_{14}$ | Cl | 6.25 | 12.5 | 100 | 25 | 25 |

The above table clearly shows that the novel amido-quaternary ammonium compounds of instant invention which contain two large aliphatic or alicyclic groups

* * * * *